United States Patent [19]

Kelm et al.

[11] Patent Number: 5,814,336

[45] Date of Patent: Sep. 29, 1998

[54] PHARMACEUTICAL DOSAGE FORM FOR COLONIC DELIVERY

[75] Inventors: Gary Robert Kelm, Cincinnati; Gary Lee Manring, Hamilton, both of Ohio

[73] Assignee: The Procter & Gamble Company, Cincinnati, Ohio

[21] Appl. No.: 719,108

[22] Filed: Sep. 24, 1996

Related U.S. Application Data

[63] Continuation of Ser. No. 442,921, May 17, 1995, Pat. No. 5,686,106.

[51] Int. Cl.⁶ ............................... A61K 9/32; A61K 9/36; A61K 9/52

[52] U.S. Cl. .................. 424/463; 424/474; 424/480; 424/482; 424/490; 424/494; 424/497

[58] Field of Search ..................................... 424/463, 474, 424/479, 480, 482, 494, 497, 461, 462

[56] References Cited

FOREIGN PATENT DOCUMENTS

| 0572942 | 8/1993 | European Pat. Off. . | |
|---|---|---|---|
| WO 95/35100 | 12/1995 | WIPO | A61K 9/48 |
| WO 96/36319 | 11/1996 | WIPO | A61K 9/22 |
| WO 96/36338 | 11/1996 | WIPO | A61K 31/44 |

*Primary Examiner*—Thurman K. Page
*Assistant Examiner*—James M. Spear
*Attorney, Agent, or Firm*—Betty J. Zea; Karen F. Clark; Jacobus C. Rasser

[57] ABSTRACT

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutically active agent incorporated into or coated on the surface of a dosage form selected from the group consisting of a spherical substrate, an elliptical substrate, a hard capsule, or a compressed tablet, with a maximum diameter of about 3 mm to about 10 mm; and b. an enteric polymer coating material;

wherein the dosage form has a smooth surface free from edges or sharp curves; the elliptical substrate and the hard capsule have a ratio of the long to short diameters of no greater than about 1.5; the therapeutically active agent is released at a point near the inlet to, or within the colon; the enteric polymer coating material begins to dissolve in an aqueous media at a pH between about 5 to about 6.3; and the enteric polymer coating material has a coating thickness of at least about 250 μm.

8 Claims, No Drawings

PHARMACEUTICAL DOSAGE FORM FOR COLONIC DELIVERY

This is a continuation of application Ser. No. 08/442,921, filed on May 17, 1995 U.S. Pat. No. 5,686,106.

TECHNICAL FIELD

The present invention relates to novel spherical unit dosage forms to release therapeutic agents at a point near the inlet to, or within the colon.

BACKGROUND OF THE INVENTION

Release of therapeutically active agents in the colon from a perorally administered dosage form is desirable in several situations, including: (1) topical treatment of diseases of the colon such as constipation, irritable bowel syndrome (IBS), Crohn's disease, ulcerative colitis, carcinomas, and infection in which systemic absorption of the therapeutic agent is neither required or desired; (2) systemic absorption of therapeutic agents such as peptides and proteins which are subject to lumenal degradation in the stomach and small intestine; and (3) systemic absorption of therapeutic agents for which peak systemic concentrations and pharmacological activity are desired at time significantly delayed from the time of peroral administration (i.e., peak plasma concentrations in the early morning just prior to arising, from a peroral dosage form ingested at bedtime). Colonic release of therapeutically active agents from a perorally administered dosage form requires that release of said agent for topical activity or systemic absorption be prevented in the stomach and small intestine, but permitted in the colon. This in turn requires design of the dosage form to be such that it takes advantage of features of the gastrointestinal tract that indicate arrival of the dosage form in the colon, relative to other portions of the gastrointestinal tract (M. Ashford and J. T. Fell, *J. Drug Targeting*, 1994, 2:241–258). Variable features include pH, ionic strength, apparent velocity, and bacterial content of the lumenal contents of the several anatomical portions of the gastrointestinal tract as well as the residence time of a pharmaceutical unit dosage form therein (M. Ashford and J. T. Fell, *J. Drug Targeting*, 1994, 2:241–258; S. S. Davis, *J. Contr. Rel.*, 1985, 2:27–38).

The residence time of pharmaceutical unit dosage forms in the stomach can be particularly variable (M. Ashford and J. T. Fell, *J. Drug Targeting*, 1994, 2:241–258). However, the small intestinal transit time of pharmaceutical unit dosage forms has been demonstrated to be relatively constant with a mean value of approximately three hours (M. Ashford and J. T. Fell, *J. Drug Targeting*, 1994, 2:241–258). Residence times in the colon are usually longer than in other portions of the gastrointestinal tract, but times within the several segments can be highly variable (M. Ashford and J. T. Fell, *J. Drug Targeting*, 1994, 2:241–258).

The pH profile of the lumenal contents of the gastrointestinal tract has also been characterized and found to be relatively consistent (D. F. Evans, G. Pye, R. Bramley, A. G. Clark, and T. J. Dyson, *Gut*, 1988, 29:1035–1041). The pH of the stomach may vary temporarily with prandial state, but is generally below about pH 2. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon.

A distinguishing feature of the colon relative to other portions of the gastrointestinal tract is the presence of exogenous bacteria. These are capable of enzymatically catalyzing reactions of which the host animal is incapable.

It has been recognized in general that dosage forms designed for colonic release may employ one of the following features to indicate arrival of the dosage form in the colon, relative to other portions of the gastrointestinal tract: (1) the generally increasing pH profile of the lumenal contents up to the ileocecal junction; (2) the relatively constant small intestinal transit time of a pharmaceutical unit dosage form (compensating for the highly variable stomach residence time); and (3) the presence of exogenous bacteria in the colon (M. Ashford and J. T. Fell, *J. Drug Targeting*, 1994, 2:241–258).

Dosage forms employing the generally increasing pH profile of the lumenal contents of the gastrointestinal tract as a design feature to indicate colonic arrival typically employ film coatings of enteric polymers. These enteric polymers are polyanionic polymers which are insoluble in water and at low pHs, but begin to dissolve at pHs of about 5. Commercially available enteric polymers begin to dissolve within the pH range of about 5 to 7.

Examples of the use of this type of rationale to design dosage forms for delivery to the colon include: U.S. Pat. No. 5,171,580, issued Dec. 15, 1992, Boehringer Ingelheim Italia, which teaches a preparation for delivery in the large intestine and especially the colon, comprising an active containing core coated with three protection layers of coatings having different solubilities. The inner layer is Eudragitg® S, with a coating thickness of about 40–120 microns, the intermediate coating layer is a swellable polymer with a coating thickness of about 40–120 microns, and the outer layer is cellulose acetate phthalate, hydroxypropyl methyl cellulose phthalate, polyvinyl acetate phthalate, hydroxyethyl cellulose phthalate, cellulose acetate tetrahydrophthalate, or Eudragit® L.

U.S. Pat. No. 4,910,021, issued on Mar. 20, 1990, Scherer Corp., which teaches a targeted delivery system wherein the composition comprises a hard or soft gelatin capsule containing an active ingredient such as insulin and an absorption promoter. The capsule is coated with a film forming composition being sufficiently soluble at a pH above 7 as to be capable of permitting the erosion or dissolution of said capsule. The film forming composition is preferably a mixture of Eudragit® L, Eudragit® RS, and Eudragit® S at specific ratios to provide solubility above a pH of 7. Coating levels above what is known in the art are not disclosed.

U.S. Pat. No. 4,432,966, issued on Feb. 21, 1984, Roussel-UCLAF, which teaches a compressed tablet with an active agent, coated with a first coating layer comprising a mixture of microcrystalline cellulose and lower alkyl ether of a cellulose film-forming organic polymer such as ethyl cellulose, and a second coating layer selected from cellulose acetylphthalate, hydroxypropyl methylcellulose phthalate, benzophenyl salicylate, cellulose acetosuccinate, copolymers of styrene and of maleic acid, formylated gelatin, salol, keratin, steraric acid, myristic acid, gluten, acrylic and methacrylic resins, and copolymers of maleic acid and phthalic acid derivatives.

Using pH as an indicator of colonic arrival of the dosage form presents some difficulties. Although the pH of the lumenal contents gradually increases from the stomach through the small intestine, the pH of the lumenal contents of the proximal portions of the colon is lower than that of the distal small intestine (ileum). This is due to the presence of short chain fatty acids produced by the action of exogenous bacteria in the colon. Therefore, a given pH value does not distinguish the colon from various portions of the small intestine. A dosage form designed to release the therapeutic agent at the pH of the proximal colon would also release the therapeutic agent at those portions of the small intestine proximal to the ileum within which the pH is similar to that of the proximal colon. Thus, the validity of the use of enteric coatings to attain colonic release has been questioned (M. Ashford and J. T. Fell, *J. Drug Targeting*, 1994, 2:241–258; M. Ashford, J. T. Fell, D. Attwood, and P. J. Woodhead, *Int. J. Pharm.*, 1993, 91:241–245; M. Ashford, J. T. Fell, D. Attwood, H. L. Sharma, and P. J. Woodhead, *Int. J. Pharm.*, 1993, 95:193–199).

Although lumenal content pH alone does not distinguish the colon from various other portions of the small intestine, pH does distinguish the stomach from the small intestine and colon. Enteric polymer coatings have been extensively used in the prior art to distinguish the stomach from the small intestine and prevent release of a therapeutic agent until the dosage form has emptied from the stomach. This use has resulted in an extensive history confirming the safety of these polymers, a large literature describing suitable processes for application of these polymers as coatings to dosage forms, and the commercial availability of a number of suitable enteric polymers.

It has been recognized that dosage forms that delay release of a therapeutic agent for a time period corresponding to the stomach and small intestine residence times will provide colonic delivery (S. S. Davis, *J. Contr. Rel.*, 1985, 2:27–38). This has been primarily based upon the reasonably constant residence time in the small intestine, assuming that the additional use of an enteric polymeric coating will compensate for variable stomach residence times by preventing activation of the time based delay mechanism until the dosage form has reached the small intestine. Proposed time delay mechanisms include those based upon slow dissolution of pH independent coatings (A. Gazzaniga, P. Iamartino, G. Maffione, and M. E. Sangalli, Proceed. 6th Int. Conf. on Pharm. Techn. (Paris) 305–313, 1992), controlled pH independent, permeation of water through a coating to activate disintegration of the dosage form by osmotic pressure (F. Theeuwes, P. L. Wong, T. L. Burkoth, and D. A. Fox, in Colonic Drug Absorption and Metabolism, P. R. Bieck, ed., Marcel Dekker, Inc., New York, Basel, Hong Kong, 137–158 (1993)) or by physical swelling (R. Ishino, H. Yoshino, Y. Kirakawa, and K. Noda, *Chem. Pharm. Bull.*, 1992, 40:3036–3041), and swelling and ejection of a plug by pH independent hydration (I. R. Wilding, hydration (I. R. Wilding, S. S. Davis, M. Bakhshaee, H. N. E. Stevens, R. A. Sparrow, and J. Brennan, *Pharm. Res.*, 1992, 9:654–657). Such approaches have not been completely satisfactory for reasons of size, reproducibility of time to release, complexity, and expense.

Although enteric polymers have a long history of commercial use and inherently compensate for variable stomach residence times, their use to provide a time based delay in therapeutic agent release based upon dissolution of an enteric polymer coating has not been advocated. This is presumably due to the variability in enteric polymer dissolution as a function of the varying pH and velocity of the lumenal contents of the small intestine and colon. However, a dosage form employing an enteric polymer to achieve colonic release based upon dissolution time of the enteric polymer coating has advantages in terms of proven safety of these polymers and commercially feasible application processes.

It is an object of the present invention to provide colonic release of therapeutic agents from a unit dosage form by employing enteric polymers as the means of delaying release of the therapeutic agent.

SUMMARY OF THE INVENTION

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutic agent incorporated into or coated on the surface of a dosage form selected from the group consisting of a spherical substrate, an elliptical substrate, a hard capsule, or a compressed tablet, with a maximum diameter of about 3 mm to about 10 mm; and b. an enteric polymer coating material;

wherein the dosage form has a smooth surface free from edges or sharp curves; the elliptical substrate and the hard capsule have a ratio of the long to short diameters of no greater than about 1.5; the therapeutic agent is released at a point near the inlet to, or within the colon; the enteric polymer coating material begins to dissolve in an aqueous media at a pH between about 5 to about 6.3; and the enteric polymer coating material has a coating thickness of at least about 250 $\mu$m.

DETAILED DESCRIPTION OF THE INVENTION

The use of enteric polymers to delay release of a therapeutic agent from a pharmaceutical unit dosage form until said dosage form has reached the colon has not been entirely successful. Reasons for the lack of success include:

a. the decrease in the pH of the lumenal contents of the proximal colon relative to the terminal small intestine (ileum) which oviates the use of pH as a recognition factor for colonic delivery as described previously;

b. the difficulty of designing an enteric polymer coating over a unit dosage form that will completely dissolve during the residence time of the dosage form in the small intestine due to the varition in pH and velocity of the lumenal contents of the small intestine and colon; and c. thin spots in the enteric polymer coating that develop over edges and sharp curves in conventional unit dosage forms resulting in premature rupture of the enteric polymer coating and release of the therapeutic agent.

The enteric polymer coated dosage forms of the present invention are designed to delay release of the therapeutic agent for a period of time approximately corresponding to the residence time in the small intestine, rather than employing a given pH value as a recognition factor for colonic arrival. This eliminates the problem introduced by the decrease in pH in the proximal colon relative to the ileum.

The inventors have discovered that the amounts of enteric polymer required to delay release of the therapeutic agent for a time approximately corresponding to the residence time in the small intestine can be determined by 1. a knowledge of the dissolution behavior of the selected enteric polymer as a function of the size of the dosage form and the pH and velocity of an aqueous medium, and 2. by an estimation of the pH and apparent velocity of the lumenal contents of the sequential anatomical segments of the small intestine and colon. Since final dissolution of the enteric coating is desired to occur in the colon, the enteric polymer comprising the coating of the unit dosage form must be selected and applied to the dosage form such that the coating will be soluble in the proximal portion of the colon, or at a maximum pH of about 6.3. As described below, the amounts of enteric polymer required to achieve the requisite delay in release of the therapeutic agent are greatly in excess of those revealed in the prior art.

It is desirable in dosage forms of the present invention that the enteric coating essentially completely dissolves prior to release of the therapeutic agent in order to assure that the predicted dissolution time for a given amount of enteric polymer coating corresponds to the time release of the therapeutic agent is delayed. This requires a relatively consistent or uniform enteric polymer film coating over the dosage forms. Thin spots in the enteric polymer coating can occur over edges and sharp curves of conventional dosage forms and can result in premature rupture of the enteric polymer coating and release of the therapeutic agent. Therefore, dosage forms of the present invention are spherical or elliptical in shape, of a nearly uniform size, with smooth surfaces essentially free from edges or sharp curves in order to facilitate the application of a enteric polymer coating of uniform thickness over each of the unit dosage forms.

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutic agent incorporated into or coated on the surface of a dosage form selected from the group consisting of a spherical substrate, an elliptical substrate, a hard capsule, or a compressed tablet, with a maximum diameter of about 3 mm to about 10 mm; and b. an enteric polymer coating material;

wherein the dosage form has a smooth surface free from edges or sharp curves; the elliptical substrate and the hard capsule have a ratio of the long to short diameters of no greater than about 1.5; the therapeutic agent is released at a point near the inlet to, or within the colon; the enteric polymer coating material begins to dissolve in an aqueous media at a pH between about 5 to about 6.3; and the enteric polymer coating material has a coating thickness of at least about 250 $\mu$m.

Preferably for a spherical substrate, an elliptical substrate, hard capsule or compressed tablet having a diameter of about 3 mm (the long diameter for the elliptical substrate or hard capsule), the minimum coating thickness is about 60 mg./cm$^2$. Preferably for a spherical or elliptical substrate, hard capsule or a compressed tablet having a diameter of about 10 mm (the long diameter for the elliptical substrate or hard capsule), the minimum coating thickness is about 30 mg./cm$^2$.

The dosage forms of the present invention are to be distinguished from controlled (sustained) release compositions which slowly release a drug active over an extended period of time and extend the duration of drug action over that achieved with conventional delivery. The dosage forms of the present invention prevent the release of the therapeutically active until the dosage form reaches the colon. The subsequent rate of release of the therapeutic agent will vary from rapid to slow depending upon the pharmacodynamic requirements of the specific therapeutic agent.

Therapeutically Active Agent

The methods and compositions of the present invention comprise a safe and effective amount of therapeutically active agent. The phrase "safe and effective amount", as used herein, means an amount of therapeutically active agent high enough to provide a significant positive modification of the condition to be treated, but low enough to avoid serious side effects (at a reasonable benefit/risk ratio), within the scope of sound medical judgment. A safe and effective amount of therapeutically active agent will vary with the particular condition being treated, the age and physical condition of the patient being treated, the severity of the condition, the duration of the treatment, the nature of concurrent therapy, the agent selected, and like factors.

Therapeutic agents suitable for incorporation into dosage forms of the present invention are those for which release in the colon or delayed release is therapeutically advantageous. These include therapeutic agents useful for topical treatment of diseases of the colon such as constipation, diarrhea, irritable bowel syndrome (IBS), Crohn's disease, ulcerative colitis, carcinomas, and infection in which systemic absorption of the therapeutic agent is neither required or desired. These include laxatives such as picosulfate and sennasides, anti-diarrheals such as loperamide, nonsteroidal anti-inflammatory drugs such as 5-amino salicylic acid, glucocorticoids such as dextramethazone, antimicrobials, especially those effective against anaerobic microbes such as methotrexate, immunosupressants such as cyclosporine A, and chemotherapeutics for treatment of carcinomas.

Certain therapeutic agents, particularly peptides and proteins, are subject to lumenal degradation in the stomach and small intestine. The colon may be a preferable site of absorption for such compounds since lumenal enzymatic activity is less in the colon (M. Mackay and E. Tomlinson, in Colonic Drug Absorption and Metabolism, P. R. Bieck, ed., Marcel Dekker, Inc., New York, Basel, Hong Kong, 137–158 (1993)). Peptides and proteins that may exhibit improved systemic bioavailability benefit when released in the colon include calcitonin, insulin, and human growth hormone. In certain cases, the peptide or protein may be formulated with a system than enhances the absorption of the macromolecule (M. Mackay and E. Tomlinson, in Colonic Drug Absorption and Metabolism, P. R. Bieck, ed., Marcel Dekker, Inc., New York, Basel, Hong Kong, 137–158 (1993)).

Colonic release is also desirable for systemic absorption of therapeutic agents for which peak systemic concentrations and pharmacological activity are desired at time significantly delayed from the time of peroral administration (i.e., peak plasma concentrations in the early morning just prior to arising from a peroral dosage form ingested at bedtime). This is particularly advantageous for conditions such as asthma, arthritis, inflammation, coronary infarction, and angina pectoris which are susceptible to diurnal rhythms (B. Lemmer, in Pulsatile Drug Delivery, R. Gurny, H. E. Junginger, and N. A. Pepas, eds, Wissenschaftliche Verlagsgesellschaft mbH, Stuttgart, 11–24 (1993)). Drugs for which daily variations in their effects have been reported in clinical studies include cardiovascularly active drugs such as beta-blockers (acebutolol, propranolol), calcium channel blockers (verapramil), and ACE inhibitors (enalapril), anticancer drugs such as cisplatin and duxorubicin, antiasthmatic drugs such as theophylline, psychotropic drugs such as diazepam, $H_1$-Anthihistamines such as terfenadine, nonsteroidal anti-inflammatory drugs such as flurbiprofen, naproxen, and piroxicam, and $H_2$-blockers such as cimetidine and ranitidine.

The therapeutically active agent may be incorporated onto the surface of or into one of the several substrates described herein in a manner consistent with the physical chemical properties of the drug and its pharmacodynamics using techniques known to those skilled in the art. It is recognized that the rate of release of the therapeutically active agent in the colon will be dependent upon the manner of incorporation of the therapeutically active agent and the nature and levels of any excipients. The rate of release should be such that the therapeutic activity of the agent is maximized.

As used herein, "excipient" means any component admixed with or co-incorporated with the therapeutically active agent onto the surface of or into the substrate. Excipients may act to facilitate incorporation of the therapeutically active agent onto or into the substrate, modify the release of the therapeutically active agent from the substrate, stabilize the therapeutically active agent, or enhance absorption of the therapeutically active agent. Excipients should be safe for their intended use at the levels employed in the formulation and compatible with the therapeutically active agent. Pharmaceutical excipients are disclosed in "Remington's Pharmaceutical Sciences," 17th Ed. (1985), pp. 1603–1644, which is incorporated herein by reference. The formulation of therapeutically active agent and excipients is selected according to criteria well known to those skilled in the art to achieve the desired release rate, stability, absorption, and facilitation of dosage form manufacture.

The Dosage Form

A safe and effective amount of therapeutically active agent is incorporated into or coated on the surface of a dosage form selected from the group consisting of a spherical substrate, an elliptical substrate, a hard capsule, or a compressed tablet, with a maximum diameter of about 3 mm to about 10 mm; wherein the dosage form has a smooth surface free from edges or sharp curves; the elliptical substrate and the hard capsule have a ratio of the long to short diameters of no greater than about 1.5.

Preferably the dosage forms of the present invention are selected from the group consisting of a soft gelatin capsule; molded sphere or ellipsoid made from any pharmaceutically acceptable excipient that can be melted or molded; a sphere prepared by coating or layering a substrate onto a seed crystal made of any inert pharmaceutically acceptable excipient; hard capsules without edges, having flat seals; and compressed tablets, wherein the dosage form has a smooth surface free from edges or sharp curves, and the elliptical substrate and the hard capsule have a ratio of the long to short diameters of no greater than about 1.5.

As used herein, "elliptical substrate" means an ellipsoid, a solid figure in which all plane surfaces are ellipses or circles, described by the equation $x^2/a^2 + y^2/b^2 + z^2/c^2$, wherein $b=c$, $a/b \leq 1.5$, and "a" is between 3 and 10 mm.

As used herein, "smooth surface free from edges or sharp curves" means that no edges exist on the dosage form sufficient to produce thin spots in the enteric coating relative to the mean coating thickness. Especially preferred dosage forms are spheres with a diameter of about 3 mm to about 8 mm; more preferably about 4 mm to about 7 mm. Preferably all of the dosage forms are of a uniform size prior to coating with the polymer coating material. Preferably, the diameters of substantially all of the spheres are within about 5%, more preferably within about 2%, of the mean diameter. The smooth surface and uniform size allow for uniform coating thickness and uniform dissolution of the polymer coating material.

The dosage form preferably consists of an inert spherical substrate prepared by coating and/or layering processes such as sugar spheres, NF. These substrates are sized prior to coating to obtain the desired uniform diameter by sieving and/or by weighing, i.e. separation by using a weight checker. Preferably, the diameters of substantially all of the spheres are within about 5%, more preferably within about 2%, of the mean diameter. They are subsequently coated with the therapeutically active agent. The therapeutically active agent is preferrably bound to the sugar sphere substrate with a water soluble, inert polymer, preferably low viscosity hydroxypropyl cellulose or hydroxypropyl methylcellulose. The ratio of the binding polymer to the therapeutically active agent is from about 1:10 to 10:1; preferably from about 1:5 to 5:1; more preferably from about 1:4 to 1:1.

The therapeutically active agent coating on the sugar sphere may be optionally overcoated with an inert, water soluble polymer, to a thickness of about 10 $\mu$m to about 50 $\mu$m; preferably about 20 $\mu$m to about 40 $\mu$m. This overcoat is referred to herein as a barrier coating. The barrier coating preferably consists of low viscosity hydroxypropyl methylcellulose. When the substrate is a sugar sphere and when the enteric polymer coating material is cellulose acetate phthalate, then preferably the dosage form also comprises a barrier coating between the therapeutically active agent and the cellulose acetate phthalate. The coating of active agent and the barrier coating may be applied to the commercially available inert spherical substrate by any number of processes known to those skilled in the art, including, but not limited to, perforated pan coating and fluid bed coating.

The dosage form may also perferably comprise an inert molded spherical or elliptical substrate. As used herein, "molding" refers to a process in which a molten or semi-solid inert, pharmaceutically acceptable material is injected into a mold cavity and allowed to solidify. The dimensions of the mold cavity thereby determine those of the substrate. Suitable materials include, but are not limited to, ingestible pharmaceutically acceptable waxes such as beeswax, paraffins, carnuba wax, triglycerides with a melting point above about 50° C. such as tristearin, and higher molecular weight polyethylene glycols with a melting point above about 50° C. The therapeutically active agent may be incorporated into the substrate during the molding process or coated onto molded substrates and optionally overcoated with a water soluble, inert polymer as described above.

A further preferred unit dosage form is a spherical or elliptical soft elastic gelatin capsule. The soft elastic gelatin capsule is filled with therapeutically active agent dissolved or suspended in a suitable vehicle compatible with the soft gelatin capsule.

A still further preferred unit dosage form is a hard capsule (i.e. starch or gelatin hard capsules) without edges, having flat seals where the long to short diameter is no greater than 1.5. An example is a starch capsule free from surfaces edges available under the trade name Capill® from Capsulgel (Greenwood, S.C.) in which the length of the long axis of the capsule is less than about 10 mm and not more than about 1.5 times greater than the short axis diameter of the capsule. The starch capsule may be filled with a solid form of therapeutically active agent as described above, or alternatively with therapeutically active agent dissolved or suspended in a suitable vehicle compatible with the capsule wall.

An additional preferred unit dosage form is a compressed spherical or elliptical tablet with a maximum diameter of about 3 to about 10 mm free from surface edges and sharp curves. The tablet is comprised of a solid form of therapeutically active agent and is compressed using conventional equipment and processes.

The Enteric Polymer Coating Material

In the compositions of the present invention, the polymer coating material prevents the release of therapeutically active agent as the dosage form passes through the upper gastrointestinal tract, including the mouth, esophagus, stomach, and small intestine, until the dosage form is near the junction between the small intestine and the colon or is in the colon. This precludes systemic absorption of therapeutically active agent from the upper gastrointestinal tract and/or dilution of the released therapeutically active agent in the contents of the upper gastrointestinal tract. Therefore, the polymer coating material, in combination with a spherical or elliptical substrate with a smooth surface, provides a method of delivering therapeutically active agent in a concentrated form to the colon.

As used herein, "enteric polymer coating material", is a material or materials which completely surround and encase the therapeutically active agent in the unit dosage form prior to oral administration. The polymer coating material of the present invention does not contain any active compound, i.e. therapeutically active agent, of the present invention. In addition the present invention does not comprise enteric coated microcrystal spheres or particles of the active compound or enteric coated granules of the active compound. Preferably, a substantial amount or all of the enteric polymer coating material is dissolved before the therapeutically active agent is released from the dosage form, so as to achieve delayed dissolution of the therapeutically active agent.

The polymer coating material is selected such that therapeutically active agent will be released at about the time that the dosage form reaches the inlet between the small intestine and the colon, or thereafter in the colon. Preferred coating materials include pH-sensitive materials, which remain intact in the lower pH environs of the stomach and small intestine, but which disintegrate or dissolve at the pH commonly found in the latter portion of the small intestine or beginning of the colon or in the colon of the patient. These polymers have a low apparent pKa range to minimize the impact of small intestinal pH variability as well as the drop in the pH across the ileo-cecal valve. The enteric polymer coating material begins to dissolve in an aqueous solution at a pH between about 5 to about 6.3.

The enteric polymer of the present invention is a polyanionic polymer that is insoluble in water and in aqueous solutions with a pH below about 5 to about 6.3. The solubility of the enteric polymer as a function of pH should be such that it is insoluble in the relatively acidic environment of the stomach, but soluble throughout most of the small intestine and colon. It is particularly important that the enteric polymer be soluble in the proximal portions of the colon where the lumenal pH is typically lower than that in the distal portions of the small intestine due to the presence of short chain fatty acids produced by the metabolic activity of bacteria residing in the colon.

The enteric polymer coating material is selected from the group consisting of cellulose acetate phthalate, cellulose acetate trimelliate, hydroxypropyl methylcellulose phthalate, hydroxypropyl methylcellulose acetate succinate, polyvinyl acetate phthalate, poly(methacrylic acid, methyl methacrylate) 1:1, poly(methacrylic acid, ethyl acrylate) 1:1, and compatible mixtures thereof, preferably cellulose acetate phthalate, poly(methacrylic acid, methyl methacrylate) 1:1, and compatible mixtures thereof, more preferably cellulose acetate phthalate. The coating thickness is at least about 250 microns, more preferably at least about 350 microns per unit dosage form. The 250 micron coating thickness is equivalent to about 30 mg./cm$^2$ (for a dosage form with about a 10 mm diameter) to about 60 mg./cm$^2$ (for a dosage form with about a 3 mm diameter.)

Specific examples of suitable polymer coating materials include the following: Eudragit® L, an anionic copolymer derived from methacrylic acid and methyl methacrylate, with a ratio of free carboxyl groups to the ester groups of approximately 1:1, and a mean molecular weight of approximately 135,000; Eudragit® L 30 D, an aqueous acrylic resin dispersion, an anionic copolymer derived from methacrylic acid and ethyl acrylate with a ratio of free carboxyl groups to the ester groups of approximately 1:1, and a mean molecular weight of approximately 250,000; (it is supplied as an aqueous dispersion containing 30% w/w of dry lacquer substance); Eudragit® L 100-55, an anionic copolymer derived from methacrylic acid and ethyl acrylate, with a ratio of free carboxyl groups to the ester groups of approximately 1:1, and a mean molecular weight greater than about 100,000; cellulose acetate phthalate or CAP®, available from Eastman Chemical; cellulose acetate trimelliate, CAT® available from Eastman Chemical; hydroxypropyl methylcellulose phthalate (USP/NF type 220824) HPMCP 50® and (USP/NF type 200731) HPMCP 55® available from Shin Etsu Chemical; polyvinyl acetate phthalate, PVAP®, available from Colorcon; hydroxypropyl methylcellulose acetate succinate, HPMCAS®, available from Shin Etsu Chemical.

A preferred polymer coating material is cellulose acetate phthalate (CAP®), wherein for diameters of about 4 to about 7 mm, the preferred coating thickness is about 350 to 1000 μm and about 250 to 800 μm, respectively.

Another preferred polymer is poly(methacrylic acid, methyl methacrylate) 1:1 (Eudragit® L), wherein for diameters of about 4 to about 7 mm, the preferred coating thicknesses is about 400 to about 1200 μm and about 300 to about 1000 μm, respectively.

The amount of enteric polymer coating on the dosage form must be sufficient such that complete dissolution of the coating does not occur until the dosage form is at a location within the gastrointestinal tract near the opening to, or within the colon, thereby releasing therapeutically active agent in the colon. This necessitates the requirement of a dosage form free from surface edges or sharp curves which will produce thin spots in a coating. The coating over such thin spots will dissolve prior to the dosage form reaching the colon, resulting in premature release of therapeutically active agent.

Transit of pharmaceutical dosage forms through the gastrointestinal tract has been characterized in the literature (i.e., M. Ashford and J. T. Fell, *J. Drug Targeting*, 1994, 2, 241–258). Gastric emptying of pharmaceutical dosage forms can be highly variable, but transit through the small intestine is relatively constant with a mean transit time of about three hours. The pH-solubility behaviors of the enteric polymers of the present invention are such that significant dissolution of the enteric polymer coating will not occur until the dosage form has emptied from the stomach, thereby eliminating the variability of gastric emptying as a factor in determining the amount of coating required to achieve release of therapeutically active agent in the colon. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon. In order to provide predictable dissolution corresponding to the small intestine transit time of about 3 hours and permit reproducible release of drug at the inlet between the small intestine and the colon, or thereafter in the colon, the coating should begin to dissolve within the pH range of the small intestine and continue to dissolve at the pH of the proximal colon. Therefore, the amount of enteric polymer coating should be such that it is substantially dissolved during the approximate three hour transit time of the small intestine.

Dissolution of enteric polymers of the present invention is influenced by the size of the dosage form, and the pH, ionic strength, and velocity of the surrounding aqueous medium. The latter three factors vary throughout the length of the small intestine and colon. In addition, the effect of these factors upon dissolution rate varies with each enteric polymer. Therefore, an important aspect of the present invention is the amount, or thickness of the enteric polymer coating that is required to delay the release of the drug until the dosage form has reached the colon. Although the requisite amount of enteric polymer will vary as a function of the size of the dosage form and the type of enteric polymer, the minimum amounts as discussed below are well in excess of those known in the art.

The more important parameters for determination of the amount of enteric polymer required to delay drug release until the dosage form has reached the colon have been found to include the pH solubility profile of the enteric polymer and the size of the dosage form. Approximate minimum amounts of enteric polymer as a function of the pH at which the polymer begins to dissolve and dosage from size are shown in the following table, Table 1. Also included are examples of enteric polymers.

TABLE 1

| Diameter (mm) | pH | Amt. Polymer (mg) | Minimum Thickness ($\mu$m) | Polymer/ Surf. Area (mg/cm$^2$) | Example Enteric Polymers |
|---|---|---|---|---|---|
| 3 | 5.0 | 23 | 520 | 81 | HPMCP ® 50 |
| 5 | 5.0 | 46 | 437 | 58 | PVAP ® |
| 10 | 5.0 | 127 | 338 | 40 | CAT ® |
| 3 | 5.5 | 22 | 511 | 79 | HPMCP ® 55 |
| 5 | 5.5 | 45 | 430 | 57 | Eudragit ® L100-55 |
| 10 | 5.5 | 125 | 332 | 40 | |
| 3 | 6.0 | 19 | 450 | 67 | Eudragit ® L |
| 5 | 6.0 | 38 | 376 | 49 | |
| 10 | 6.0 | 108 | 290 | 34 | |
| 3 | 6.2 | 16 | 390 | 56 | CAP ® |
| 5 | 6.2 | 33 | 326 | 41 | |
| 10 | 6.2 | 92 | 250 | 29 | |

The enteric polymer coating material may by applied to the substrate as a solution in a pharmaceutically acceptable solvent such as ethanol, acetone, isopropanol, ethyl acetate, or mixtures thereof; as an aqueous solution buffered with ammonium hydroxide, or as a fine dispersion in water using any number of processes known to one skilled in the art, including but not limited to, perforated pan coating and fluid bed coating.

To enhance the elasticity of the coating materials, preferably the coating material of the present invention also comprises a plasticizer. Appropriate plasticizers include polyethylene glycols, propylene glycols, dibutyl phthalate, diethyl phthalate, tributyl citrate, tributyrin, butyl phthalyl butyl glycolate (Santicizer® B-16, from Monsanto, St. Louis, Mo.), triacetin, castor oil and citric acid esters; preferably the plasticizer is dibutyl phthalate or triethyl citrate. These plasticizers are present in an amount to facilitate the coating process and to obtain an even coating film with enhanced physical stability. Generally the coating material comprises from about 0% to about 50% of a plasticizer, preferably from about 0% to about 25%, more preferably about 10% to about 20%, by weight of the polymer.

For cellulose acetate phthalate, the plasticizer is preferably diethyl phthalate, dibutyl phthalate, tributyl citrate, tributyrin, butyl phthalyl butyl glycolate or triacetin.

In addition, to facilitate the coating process, the coating material may also comprise inert solid particulates. Preferred inert solid particulates include talc and titanium dioxide.

The selections of optional plasticizer, optional inert solid particulate, and levels thereof, coating formulation type (solvent, ammoniated aqueous solution, or aqueous dispersion), and process are based upon the specific enteric polymer used and the type of dosage form used according to criteria known to those skilled in the art.

Method of Making

The enteric polymer coating material is generally applied onto the dosage forms as solutions in organic solvents. The solvents commonly employed as vehicles are methylene chloride, ethanol, methanol, isopropyl alcohol, acetone, ethyl acetate and combinations thereof. The choice of the solvent is based primarily on the solubility of the polymer, ease of evaporation, and viscosity of the solution.

Some polymers are also available as aqueous systems. Currently, three aqueous enteric polymer coatings are available for commercial use in the United States. These are Eudragit® L30D (methacrylic acid-ethyl acrylate acid ester copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Unlike organic solutions, these aqueous-based systems can be prepared at high concentration without encountering high viscosity. Also, these aqueous systems do not have the problems associated with the organic systems such as flammability, toxicity of the residual solvent in the dosage form, etc.

Coating can be achieved by methods known to one skilled in the art such as by using fluidized bed equipment, perforated pans, a regular pharmaceutical pan, compression coating, etc. by continuous or short spray methods, or by drenching.

Methods for coating dosage forms with cellulose acetate phthalate are disclosed in Spitael, J. et al., "Enteric Coating using Cellulose Acetate Phthalate", *Manuf. Chem.*, Vol. 57, Issue 8, August 1986 (p. 35, 37), which is incorporated herein by reference.

The following non-limiting examples provide typical formulations for compositions of the present invention.

EXAMPLE 1

A dosage form of the following formulation is prepared as described below:

| Substrate | | Barrier Coat | | Enteric Coat | |
|---|---|---|---|---|---|
| Component | Wt. (mg) | Component | Wt. (mg) | Component | Wt. (mg) |
| Sugar Sphere, USP | 212 | HPMC, USP[1] | 5 | CAP, NF[2] | 70 |
| Dextramethasone | 3 | | | Dibutyl Phthalate | 18 |
| HPMC, USP[1] | 1 | | | | |

[1]Hydroxypropyl Methylcellulose, USP. Methocel ® E15LV, Dow Chemical.
[2]Cellulose Acetate Phthalate, NF, CAP ®, Eastman Chemical.

Substrate

Dextramethasone is dispersed in water at a level of 2.7% by weight with 0.9% by weight HPMC as a binding polymer and sprayed onto sugar spheres (6.53–6.63 mm diameter) in a perforated pan coater maintaining an outlet air/bed temperature of about 40° C.

Barrier Coat

HMPC is dissolved in water to produce a 4% by weight solution which is coated on the substrates described above in a perforated pan coater maintaining an outlet air/bed temperature of about 40° C.

Enteric Coat

CAP and dibutyl phthalate are dissolved in a 1:1 solution of ethanol and acetone such that the total solids content is 12.5% by weight (10% CAP, 2.5% dibutyl phthalate). The resulting solution is coated onto the barrier coated substrates above in a perforated pan coater maintaining an outlet air/bed temperature of about 30° C.

EXAMPLE 2

A dosage form of the following formulation is prepared as described below:

| Substrate | | Enteric Coat | |
|---|---|---|---|
| Component | Wt. (mg) | Component | Wt (mg) |
| Medium Chain Triglyceride[1] | 63 | CAP, NF[2] | 70 |
| Polyoxyl 35 Castor Oil, NF | 2 | Dibutyl Phthalate | 18 |
| Poloxamer 182 | 20 | | |
| Propanolol Base | 15 | | |
| #3 Spherical Soft Elastic Gelatin Capsule | N/A | | |

[1]Captex ® 300, ABITEC Corp.
[2]Cellulose Acetate Phthalate, NF, CAP ®, Eastman Chemical.

Substrate

Medium chain triglyceride, polyoxyl 35 castor oil, and poloxamer 182 are blended to produce a solution of a self-emulsifying lipid. Propanolol base is subsequently dissolved in the self-emulsifying lipid vehicle which is then filled into a #3 soft elastic gelatin capsule at a level of 100 mg using conventional equipment.

Enteric Coat

CAP and dibutyl phthalate are dissolved in a 1:1 solution of ethanol and acetone such that the total solids content is 12.5% by weight (10% CAP, 2.5% dibutyl phthalate). The resulting solution is coated onto the filled soft elastic gelatin substrates above in a perforated pan coater maintaining an outlet air/bed temperature of about 30° C.

EXAMPLE 3

A dosage form of the following formulation is prepared as described below:

| Substrate | | Enteric Coat | |
|---|---|---|---|
| Component | Wt. (mg) | Component | Wt (mg) |
| Sugar Sphere, USP | 50 | Eudragit L[2] | 75 |
| Mesalamine | 200 | Dibutyl Phthalate | 15 |
| HPMC, USP[1] | 50 | Red Ferric Oxide | 12 |
| | | Talc, USP | 20 |

[1]Hydroxypropyl Methylcellulose, USP. Methocel ® E15LV, Dow Chemical.
[2]Poly(methacrylic acid, methyl methacrylate) 1:1, Eudragit ® L, Rohm Tech.

Substrate

Mesalamine is coated onto sugar spheres (2.9–3.1 mm diameter) using a binding solution of 10% by weight HPMC in water in a CF Granulator (Vector Corp.).

Enteric Coat

Eudrait® L and dibutyl phthalate are dissolved in a solution of isopropanol, acetone, and water (37:9:1) at levels of 8.0% and 1.6% (total weight percent), respectively. Red ferric oxide and talc are then suspended in the solution at levels of 1.2% and 2.1% by weight, respectively. The resulting mixture is coated onto the barrier coated substrates above in a perforated pan coater maintaining an outlet air/bed temperature of about 30° C.

EXAMPLE 4

A dosage form of the following formulation is prepared as described below:

| Substrate | | Enteric Coat | |
|---|---|---|---|
| Component | Wt. (mg) | Component | Wt (mg) |
| Oleic Acid | 30 | CAP, NF[1] | 70 |
| Polyoxyl 60 Hydrogenated Castor Oil, NF | 69.5 | Dibutyl Phthalate | 18 |
| Salmon Calcitonin | 0.5 | | |
| #3 Spherical Soft Elastic Gelatin Capsule | N/A | | |

[1]Cellulose Acetate Phthalate, NF, CAP, Eastman Chemical

Substrate

Oleic acid and polyoxyl 60 hydrogenated castor oil are blended to produce a solution. Salmon calcitonin is subsequently dispersed in the self-emulsifying lipid vehicle which is then filled into a #3 soft elastic gelatin capsule at a level of 100 mg using conventional equipment.

Enteric Coat

CAP and dibutyl phthalate are dissolved in a 1:1 solution of ethanol and acetone such that the total solids content is 12.5% by weight (10% CAP, 2.5% dibutyl phthalate). The resulting solution is coated onto the filled soft elastic gelatin substrates above in a perforated pan coater maintaining an outlet air/bed temperature of about 30° C.

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of a therapeutically active agent incorporated into or coated on the surface of a dosage form selected from the group consisting of a spherical substrate, an elliptical substrate, a starch or gelatin hard capsule, or a compressed tablet, with a maximum diameter of about 3 mm to about 10 mm; and b. a single enteric polymer coating which begins to dissolve in an aqueous media at a pH between 5 to 6.3 and compatible mixtures thereof, having a coating thickness of at least about 250 µm, and which provides that the therapeutically active agent is released at a point near the inlet to, or within the colon;

wherein the dosage form has a smooth surface free from edges or sharp curves; the elliptical substrate and the hard capsule have a ratio of the long to short diameters of no greater than about 1.5.

2. The composition of claim 1 wherein the therapeutically active agent is selected from the group consisting of picosulfate, sennosides, anti-diarrheals, nonsteriodal anti-inflammatory agents, glucocorticoids, antimicrobials, immunosupressants, chemotherapeutics, peptides, proteins, beta blockers, calcium channel blockers, ACE inhibitors, H2-blockers, antiasthmatic agents, and antihistamines.

3. The composition of claim 1 wherein the dosage form is selected from the group consisting of a soft elastic gelatin capsule; a molded spherical substrate or elliptical substrate made from any pharmaceutically acceptable excipient that can be melted or molded; and a spherical substrate or elliptical substrate prepared by coating or layering a substrate onto a seed crystal made of any inert pharmaceutically acceptable excipient.

4. The composition of claim 3 wherein the dosage form is a soft elastic gelatin capsule or a sugar sphere.

5. The composition of claim 1 wherein the enteric polymer coating material is selected from the group consisting of cellulose acetate phthalate, cellulose acetate trimelliate, hydroxypropyl methylcellulose phthalate, hydroxypropyl methylcellulose acetate succinate, polyvinyl acetate phthalate, poly(methacrylic acid, methyl methacrylate) 1:1, poly(methacrylic acid, ethyl acrylate) 1:1, and compatible mixtures thereof.

6. The composition of claim 5 wherein the enteric polymer coating material is cellulose acetate phthalate.

7. The composition of claim 6 wherein the enteric polymer coating material is plasticized.

8. A method for providing delivery of a therapeutically active agent to the colon of a human or lower animal by administering a safe and effective amount of the composition of claim 1 perorally.

* * * * *